United States Patent

Patterson et al.

[11] Patent Number: 5,549,576
[45] Date of Patent: Aug. 27, 1996

[54] VASCULAR INTRODUCER VALVE WITH PROXIMAL SELF-LUBRICATION

[75] Inventors: Frank Patterson, Exeter, N.H.; John Zhang, Burlington; George Purtell, Westford, both of Mass.

[73] Assignee: C. R. Bard, Inc., Murray Hill, N.J.

[21] Appl. No.: 58,594

[22] Filed: May 7, 1993

[51] Int. Cl.⁶ ........................................ A61M 5/00
[52] U.S. Cl. .................... 604/247; 604/256; 604/167; 604/265; 251/149.1
[58] Field of Search ........................ 604/246, 247, 604/249, 264, 265, 280, 283, 33, 90, 167, 905; 251/149.1

[56] References Cited

U.S. PATENT DOCUMENTS

| | | |
|---|---|---|
| 4,610,674 | 9/1986 | Suzuki et al. . |
| 4,649,904 | 3/1987 | Krauter et al. .................. 604/167 |
| 4,798,594 | 1/1989 | Hillstead ........................ 604/167 |
| 4,857,062 | 8/1989 | Russell . |
| 4,886,507 | 12/1989 | Patton et al. . |
| 4,895,565 | 1/1990 | Hillstead . |
| 4,932,633 | 6/1990 | Johnson et al. .................. 604/905 |
| 4,960,412 | 10/1990 | Fink . |
| 5,000,745 | 3/1991 | Guest et al. . |
| 5,009,391 | 4/1991 | Steigerwald ..................... 604/247 |
| 5,059,186 | 10/1991 | Yamamoto et al. ............... 604/265 |
| 5,084,023 | 1/1992 | Lemieux .......................... 604/249 |
| 5,098,393 | 3/1992 | Amplatz et al. .................. 604/167 |
| 5,104,389 | 4/1992 | Deem et al. ...................... 604/167 |
| 5,114,408 | 3/1992 | Fleischhaker . |
| 5,125,910 | 6/1992 | Freitas ............................ 604/249 |
| 5,167,637 | 12/1992 | Okada et al. .................... 251/149.1 |
| 5,195,980 | 3/1993 | Catlin . |
| 5,211,634 | 5/1993 | Vaillancourt .................... 251/149.1 |
| 5,242,413 | 9/1993 | Heiliger . |
| 5,242,428 | 9/1993 | Palestrant ........................ 604/265 |
| 5,254,097 | 10/1993 | Schock et al. . |
| 5,267,982 | 12/1993 | Sylvanowicz . |
| 5,273,545 | 12/1993 | Hunt ............................... 604/167 |

FOREIGN PATENT DOCUMENTS

| | | |
|---|---|---|
| 0308815 | 3/1989 | European Pat. Off. . |
| 344907 | 12/1989 | European Pat. Off. . |
| 0442194A2 | 8/1991 | European Pat. Off. . |
| WO93/25252 | 12/1993 | WIPO . |

Primary Examiner—Randall L. Green
Assistant Examiner—Chalin Smith
Attorney, Agent, or Firm—Bookstein & Kudirka, P.C.

[57] ABSTRACT

An improved self-lubricating catheter and guidewire introducer is provided with a reservoir containing lubrication fluid located proximally of a sealing gasket in a modified end cap. An improved self-sealing gasket provides hemostasis while reducing the force required to move a catheter or guidewire positioned within the gasket.

7 Claims, 2 Drawing Sheets

VASCULAR INTRODUCER VALVE WITH PROXIMAL SELF-LUBRICATION

FIELD OF THE INVENTION

This invention relates to improvements in vascular catheter introducers used for the introduction, manipulation and removal of catheters, guidewires and other instruments from a patient's vascular system for angiographic, angioplastic and other procedures. More particularly, the invention relates to an improved introducer which is provided with a reservoir of lubricating fluid proximally of a self-sealing gasket to increase the ease of movement of catheters, guidewires and other instruments over a number of catheter and guidewire exchanges. The invention also provides an improved self-sealing gasket which maintains hemostasis while easing the force of movement of a catheter, guidewire or other instrument passed through the gasket.

BACKGROUND OF THE INVENTION

This invention relates to improvements in the ease of movement and manipulation of catheters, guidewires and other instruments passed through catheter introducers. Catheter introducers are devices which may be placed into a patient's vascular system for angiographic, angioplastic and other medical procedures. A catheter introducer generally consists of a distally extending tube-like portion which is inserted, partially of wholly, within the patient's vascular system or other body part. The tube-like portion has a housing on the proximal end of the tube-like portion. The housing is intended to remain outside the patient's body and is provided with one or more self-sealing gaskets to enable the catheters, guidewires or other instruments (such as needles and dilators) to be inserted through the gasket, then through the tube-like portion and subsequently into the patient's vascular system or other body portion.

The catheter introducer may remain in the patient's vascular system for a period of time during a anglographic or angioplasty procedure, during which time various needles, dilators, guidewires and catheters may be inserted, manipulated and removed from the introducer. During these activities the catheter, guidewire or other instrument is moved through the self-sealing gasket contained in the proximal fitting. The self-sealing gasket ideally has the dual desirable characteristics of providing a tight seal around the instrument inserted through the gasket to prevent the escape of blood or other fluids from the patient while at the same time not being so tight that the free movement of the instrument is impeded. Ease of movement is important because, as is well known in the art, a physician performing a procedure will rely on the "feel" of the catheter or guidewire as it is advanced through the patient's vascular system. The "feel" is important because the feedback a physician receives is used to guide the guidewire or catheter through the patient's sometimes tortuous vascular system. Thus, a compromise must usually be struck between sealing ability and ease of movement.

Prior art devices have attempted to address the desirable characteristics of sealing ability and ease of movement by providing lubrication of the self-sealing gasket by impregnating the gasket with a lubricating oil. U.S. Pat. No. 4,798,594 to Hillstead discloses impregnating the gasket with a free silicone lubricating fluid. While this method may be somewhat effective over the short term, the amount of lubricating fluid contained within the gasket will dissipate after only a few catheter or guidewire exchanges as the catheter or guidewire picks up an amount of oil and depletes the oil within the gasket. In a anglographic or angioplasty procedure, for example, there may be as many as 7 or 8 exchanges. The limited amount of lubricating fluid in a gasket similar to the Hillstead design results in the fluid being depleted after only 3 or 4 exchanges, thus decreasing the ease of movement in subsequent exchanges.

Other prior art devices have included a lubricating fluid-containing portion in the proximal housing. An example of this arrangement is illustrated in U.S. Pat. No. 5,104,389 to Deem et al. Deem et al. disclose a catheter introducer housing which has a foamed elastomer material located distally of a self-sealing gasket. The patent discloses introducing a hydrophilic lubricant material on the elastomeric partition member or gasket as well as on the foamed elastomer material.

Another prior art device, U.S. Pat. No. 5,098,393 to Amplatz et al., discloses a catheter introducer in which the housing includes a sponge material which contains a lubricating fluid. The catheter or guidewire, as in Deem et al., passes through the sponge or foamed material and picks up lubricating fluid to ease the movement of such instruments. While both Deem et al. and Amplatz et al. provide a means for lubricating instruments passed through the gaskets, the presence of a foamed material or sponge would impede the movement of such instrument and negate to some extent the benefit received by using lubricating fluid. In addition, the location of the lubricating fluid distally of the gasket does not optimally lubricate a catheter or guidewire which is inserted through the proximal end of the gasket because there is no lubricating fluid to ease the entry of such catheter or guidewire at the proximal end of the gasket.

In yet another prior art device, illustrated by U.S. Pat. No. 4,649,904 to Krauter et al., an endoscopic seal discloses the use of lubricant in a cavity located between a first outer and second inner distally positioned seal or gasket to facilitate the passage of a biopsy forceps or other tool through the outer and inner seals. In Krauter et al., as in Deem et al. and Amplatz et al., the source of lubricating fluid is located distally of the outer surface of the gasket such that a catheter or guidewire entering the hub or fitting is not lubricated as it passes through the first gasket. In addition, the Krauter et al. device requires two seals which act to contain the lubricating fluid, and the fluid is subject to escape into the body of the endoscope if an instrument is passed through the first and second seal or gasket.

Thus, while prior art devices recognizes that lubrication of catheters and guidewires is desirable, each of the prior art devices has certain deficiencies discussed above. It is among the general objects of the invention to provide an improved catheter introducer which provides for efficient lubrication of the gasket over a number of catheter and guidewire exchanges by providing a reservoir of lubricating fluid proximally of the gasket.

SUMMARY OF THE INVENTION

Proximal self-lubrication of a gasket in a catheter or other vascular introducer is provided in the present invention by providing a reservoir containing lubricating fluid in a modified end cap at the proximal end of the introducer housing. The end cap in the housing, located proximally of a self-sealing gasket, provides a space or reservoir for the retention of lubricating fluid. The reservoir is sized to contain an amount of lubricating fluid sufficient for a number of catheter or guidewire exchanges. The reservoir is located in a relatively protected position so that the lubricating fluid will neither dry out over a extended period of storage of the catheter introducer nor will it escape from the introducer end cap when the introducer is heat sterilized. In addition, the positioning of the reservoir proximally of the gasket causes a catheter or guidewire to encounter the lubricating fluid and become lubricated prior to entering the self-sealing gasket, so that the catheter or guidewire is immediately lubricated and entry is eased. The improved end cap may take the form of a number of embodiments, including embodiments which permit the storage of greater amounts of lubricating fluids and embodiments which allow for venting of air as lubricating fluid is injected into the lubricating fluid reservoir.

The improved catheter introducer also incorporates a novel self-sealing gasket which maintains hemostasis over a wide range of catheter and guidewire sizes (diameters) while being thinner than prior art gaskets and providing greater ease of guidewire and catheter movement. The improved gasket may be effectively utilized in conjunction with the self-lubricating catheter introducer of the present invention or may be used effectively in other prior art introducer housings.

It is among the general objects of the invention to provide an improved lubricated catheter introducer which has a reservoir for lubricating fluids.

It is a further object of the present invention to provide a lubrication fluid reservoir sufficient for lubricating a self-sealing gasket over a relatively large number of catheter and guidewire exchanges.

It is another object of the present invention to provide an improved end cap for the housing of a catheter introducer containing a reservoir positioned proximally of a self-sealing gasket to lubricate the gasket and various instruments passed through the gasket.

It is yet another object of the present invention to provide a gasket which may be utilized in combination with the improved self-lubricating catheter introducer to provide better ease of movement while maintaining hemostasis of catheters, guidewires or other instruments passed through the gasket.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 1:
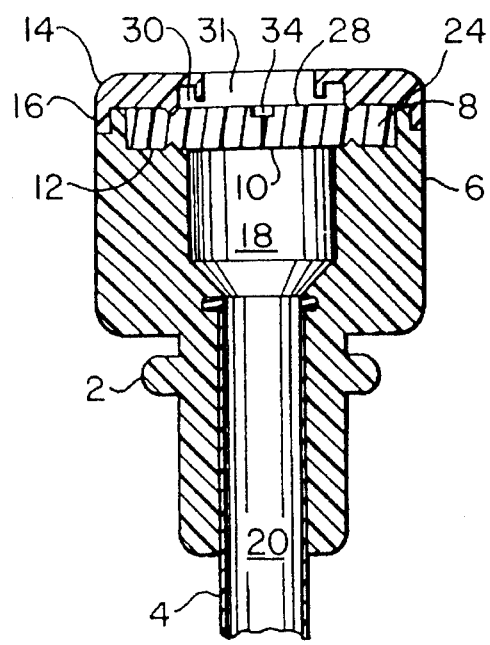
FIG. 1 is an illustration of a first embodiment of the present invention in the housing of a catheter introducer sectioned to illustrate the internal structure of the housing.

FIG. 1 illustrates a catheter introducer 2 which has a distal sheath portion 4 shown in part. The distal sheath portion 4 is a tube-like hollow shaft which extends for a distance distally of a hub or housing portion 6. The distal portion, as is well known to those skilled in the art, is the portion which is positioned wholly or partly into the patient's body while the housing portion remains outside the patient's body. The housing portion contains a gasket 8 in the embodiment. The gasket 8 is of the self-sealing type and may be of many varieties. One gasket which may be utilized in the housing 6 is described in pending application Ser. No. 07/817,941, filed Jan. 2, 1992), entitled "Self-Sealing Guidewire and Catheter Introducer", now U.S. Pat. No. 5,304,156, the disclosure of which is incorporated herein.

The gasket 8 is seated and supported on its distal surface 10 on a circumferential shoulder 12. An end cap 14 is fixed to the proximal end 16 of the housing 6. The end cap 14 has an aperture 16 for receiving catheters, guidewires and other instruments which may be passed through the gasket 10, through the interior 18 of the housing and then through the interior 20 of the distal portion 4 of the introducer in the conventional manner. A circumferential lip 22 shown best in FIGS. 2 and 3 may be provided to mate with a receiving portion 24 on the proximal end 16 of the housing 6.

Alternatively, a flush engagement of the housing and the end cap or other suitable arrangement to cause abutment of the end cap 14 and the proximal end of housing 6 may be provided. The end cap and housing may be joined by suitable gluing or welding using techniques known to those skilled in the art.

Figure 2:
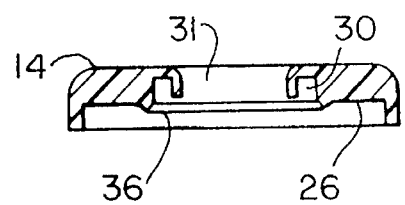
FIG. 2 is cross-sectional illustration of one embodiment of an end cap on the catheter introducer housing of the present invention.
Figure 3:
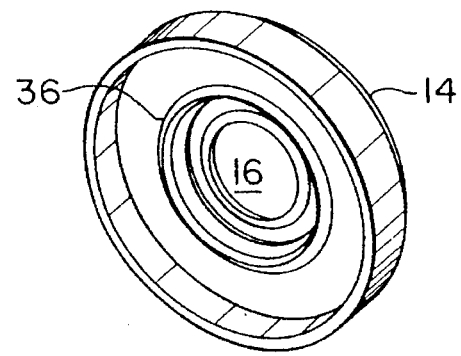
FIG. 3 is another view of the end cap of FIG. 2 as viewed from the inside of the end cap and illustrating the reservoir for lubricating fluid.

An inner annular surface 26 abuts the periphery of outer surface 28 of the gasket 10 and retains the gasket in position in conjunction with the circumferential shoulder 12. Located distally of the aperture 16 is an annular space 30 as illustrated in FIGS. 1 and 2. An annular space 30 is bounded by a ring 36 which engages the outer surface 28 of the gasket 8. As may be appreciated from FIG, 1, the space 30 is bounded on its distal end by gasket 10 and on its proximal end by depending lip portion 32 surrounding aperture 16. Lip contacts or nearly contacts the gasket surface 28 to seal in the lubricating fluid. The annular space 30 surrounding the central space 31 may, in the embodiment of FIG. 1, be filled with a lubricating fluid such as Dow Corning 360 Medical Fluid, a polydimethyisiloxane fluid, Krytox No. 16256 available from Dupont Company, Fomblin Fluids YR and Z15, available from Montedison Company, U.S.A., DEM-NUM S-100 available from Daikin, Inc., ZDOL-2000 available from Austimont Company, or any other suitable polyperfluoroether liquid.

In the embodiment illustrated in FIG. 1, the lubricating fluid is injected by conventional means during assembly largely into the annular space 30. Because the fluid is relatively viscous, the fluid will remain in the annular space 30 and not migrate out of that area. The reservoir illustrated in the embodiment of FIG. 1 may be in the range of 0.0005 to 0.0012 cubic inch. The fluid resists migration out of the annular area 30 even when exposed to elevated shipping or sterilization temperatures (in, for example, the vicinity of 140 degrees F) because of the physical containment of the fluid in the annular space 30.

In operation, when a guidewire or catheter to be inserted into the patient's vascular system is pressed against the central aperture disposed at the center of the surface 28 of the gasket 8. The gasket, in addition to the central aperture 34, may have a cut made through from the surface 28 to the inner surface 10 to allow for the passage of instruments through the gasket. Such type of gasket is described in pending Ser. No. 07/817,941 mentioned above. The gasket, which is of a suitable elastomeric material known to those skilled in the art will be deflected in a distal direction (towards the tube 4 and away from the end cap 14). This action causes the lubricating fluid to migrate away from under the space 30 towards the central aperture, coating the guidewire or catheter as it moves through the gasket.

In the embodiment of FIG. 1, tests have been made which compare the extent to which the addition of the reservoir for lubricating fluid of the present invention lessens the force required to move a 7 or 8 French size catheter through the gasket 8. In the absence of any lubricating fluid, the amount of force required to move the catheter is approximately 0.6 pound. If the gasket itself is lubricated but no lubricating fluid is present in the space 30, the force required to move the catheter is approximately 0.3 pound. If the annular space 30 forming the reservoir of lubricating fluid has a volume of approximately 0.0004 cubic inch, the force required to move the catheter is approximately 0.22 pound, and if the volume is increased to approximately 0.0008 cubic inch of lubricating fluid, the required force decreases to approximately 0.18 pound. Thus, the presence of such a volume of lubricating fluid significantly decreases the force required to move a catheter through the gasket 8.

Figure 4:
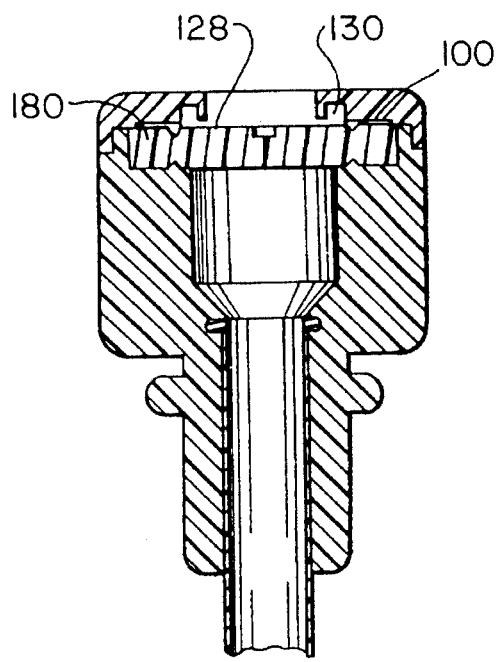
FIG. 4 is an illustration of a second embodiment of the present invention in the housing of a catheter introducer sectioned to illustrate the internal structure of the housing.
Figure 5:
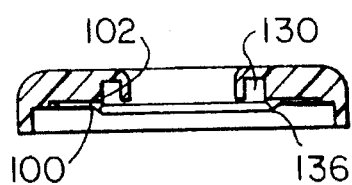
FIG. 5 is cross-sectional illustration of an end cap on the catheter introducer housing of the embodiment of FIG. 4 of the present invention.
Figure 6:
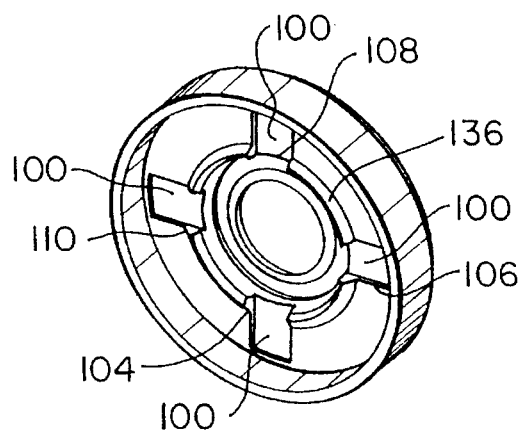
FIG. 6 is another view of the end cap of FIG. 5 as viewed from the inside of the end cap and illustrating the reservoir for lubricating fluid.

FIGS. 4 through 6 illustrate a second embodiment of that shown in FIG. 1. The second embodiment differs from the first-described embodiment with the addition of a number of additional reservoirs 100 which communicate with the annular space 130. The annular space 130 is bounded by the ring 136 which presses against the outer surface 128 of the gasket 180. The ring 136 is broken at openings 104, 106, 108 and 110 to facilitate communication of the additional reservoirs 100 with the annular space 130. In this embodiment, the additional reservoirs provide additional storage for lubricating fluid. As the lubricating fluid is dissipated from the annular space 130, the lubricating fluid contained in the additional reservoirs will enter the space 130 for lubrication of catheters and guidewires. The openings 104, 106, 108 and 110 are chosen such that the lubricating fluid will flow out of the reservoirs as the fluid is depleted but not so large as to cause flow out during storage of the introducer.

Figure 7:
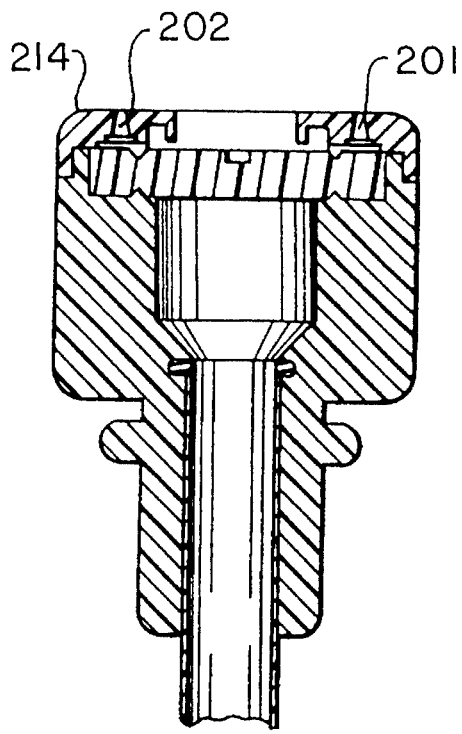
FIG. 7 is an illustration of a third embodiment of the present invention in the housing of a catheter introducer sectioned to illustrate the internal structure of the housing.
Figure 8:
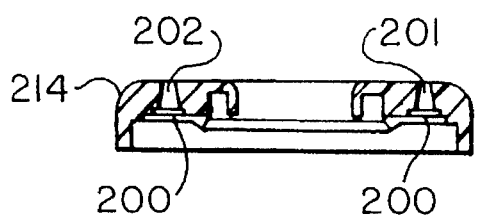
FIG. 8 is cross-sectional illustration of an end cap on the catheter introducer housing of the embodiment of FIG. 7 of the present invention.
Figure 9:
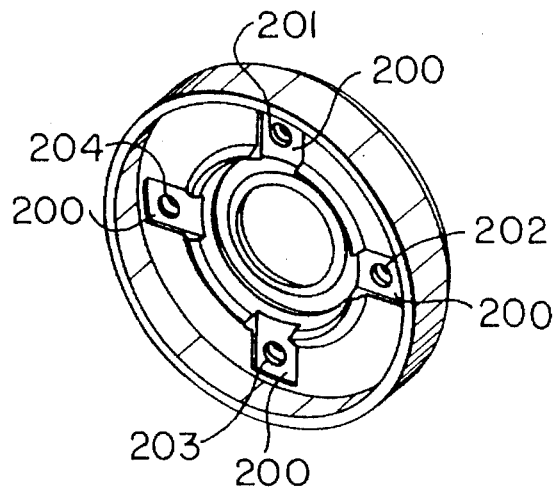
FIG. 9 is another view of the end cap of FIG. 8 as viewed from the inside of the end cap and illustrating the reservoir for lubricating fluid.

FIGS. 7 through 9 illustrate a third embodiment which is identical to the second embodiment but in which the end cap 214 has formed or drilled through the end cap a number of holes 201, 202, 203 and 204 from the proximal end of the end cap 214 (as best seen in FIG. 8) to the additional reservoirs 200. The holes, which may be any suitable number, serve the purpose of retaining even more lubricating fluid than the embodiment of FIG. 4 as well as to ease filling of the reservoirs 200 by allowing entrapped air to escape as it is displaced by fluid. The size and shape of the holes may be chosen as needed to prevent the escape of fluid from the end cap.

Figure 10:
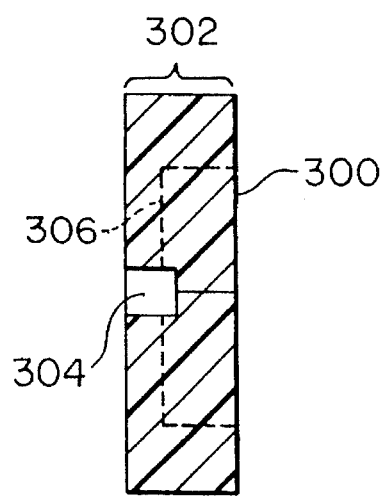
FIG. 10 is a cross-sectional view of the gasket of the present invention which may be used in the embodiments of FIGS. 1, 4 and 7.

Turning now to FIG. 10, this figure illustrates a form of a gasket which may be utilized as the gasket in each of the three illustrated embodiments. The gasket 300 is essentially similar to the gasket disclosed in copending patent application Ser. No. 07/817,941 identified above. The gasket 300 differs from the gasket in the referenced copending application in that the thickness 302 of the gasket 300 is on the order of approximately 0.055 inch. In addition, the central aperture 304, although of the same diameter as in the above-referenced patent application, is of a depth of 0.020 inch in view of the thinner thickness of the gasket 304. Furthermore, slits 306 extend through 0.041 inch of the 0.055 inch thickness and thus extend through and into the central aperture 304. It has been found that by extending the slits through and into the central region that the central aperture is weakened by the presence of a slit region within the central aperture. This allows the central aperture to "give way" when a large catheter is forced through the central aperture despite the diameter of the catheter being greater than that of the central aperture (which may have a diameter of 0.029 inch). In this manner, the central aperture will seal around a small diameter guidewire as well as a larger diameter catheter.

The gasket 300, being relatively thinner, lessens the amount of force required for catheter movement compared with a similar but thicker gasket while maintaining hemostasis. It is somewhat common in angiography and angioplasty procedures for there to be a hiatus between procedures after the catheter introducer has been placed in the patient's vascular system. For example, the introducer may be placed in a patient's system to perform angiographic testing to locate any obstruction in the patient's arteries. If such obstructions have been found, and a angioplasty procedure scheduled the next day, it is inconvenient to remove the catheter introducer and reinsert another introducer the following day. Instead, the introducer is left in place with an obturator in place of the catheter to prevent the escape of blood. In catheter introducers of thicknesses thinner than the 0.055 inch, the obturator may deform the gasket, due to its thinness. The gasket will then be unable to maintain hemostasis during the angioplasty procedure. With the approximately 0.055 inch thick gasket, however, the ability to maintain hemostasis is retained despite the presence of an obturator.

It should be understood that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. An introducer adapted to be inserted into a patient's blood vessel comprising:

a housing having a proximal end and a distal end and an introducer sheath extending distally from the distal end of the housing, the sheath being adapted to be inserted into a patient's blood vessel, the housing having an opening at the proximal end thereof;

a gasket mounted in the proximal end of the housing and adapted to enable passage of a medical instrument therethrough, the gasket having a proximal surface;

an end cap mounted to the housing proximally of the gasket to retain the gasket within the housing;

the end cap having a central opening to expose the proximal surface of the gasket at the opening; and, an annular lip extending between the end cap and the proximal surface of the gasket and defining, in cooperation with the end cap and the gasket, an annular space about the central opening to form a reservoir for retaining lubricating fluid to lubricate medical instruments inserted through the gasket.

2. An introducer adapted to be inserted into a patient's blood vessel comprising:

a housing having a proximal end and a distal end and an introducer sheath extending distally from the distal end of the housing, the sheath being adapted to be inserted into a patient's blood vessel, the housing having an opening at the proximal end thereof;

a gasket mounted in the proximal end of the housing and adapted to enable passage of a medical instrument therethrough, the gasket having a proximal surface;

an end cap mounted to the housing proximally of the gasket to retain the gasket within the housing;

the end cap having a central opening to expose the proximal surface of the gasket at the opening; and, the end cap having a distally extending lip about the end cap opening that defines, in cooperation with the proximal surface of the gasket, an annular space to form a reservoir for retaining a lubricant to lubricate medical instruments inserted through the gasket.

3. An introducer as defined in either one of claims 1 or 2 wherein the gasket comprises a self-sealing, one piece, resilient gasket having a distal surface and a central aperture in the proximal surface, the aperture being defined by a circumferential wall and extending a predetermined depth into the gasket, the distal surface being formed with a plurality of radially extending slits, the depth of the slits extending into the surrounding circumferential wall defining the central aperture, the central region of the slits overlapping the central aperture and defining a plurality of flaps normally closing the aperture and, the central aperture and the slits being dimensioned to seal a wide range of guidewires or catheters having differing diameters extended therethrough.

4. An introducer as defined in claim 3 wherein the reservoir contains a lubricating fluid.

5. A gasket as defined in claim 4 wherein the fluid is of sufficient viscosity to resist migration out of the reservoir when exposed to temperatures elevated from ambient.

6. An introducer as defined in either one of claims 1 or 2 further comprising the reservoir containing lubricating fluid.

7. An introducer as defined in claim 6 wherein the fluid is of sufficient viscosity to resist migration out of the reservoir when exposed to temperatures elevated from ambient.

* * * * *